United States Patent [19]

Olsen

[11] Patent Number: 4,813,789
[45] Date of Patent: Mar. 21, 1989

[54] NEAR-FIELD RADIO WAVE DOSIMETRY

[75] Inventor: Richard G. Olsen, Pensacola, Fla.

[73] Assignee: The United States of America as represented by the Secretary of the Navy, Washington, D.C.

[21] Appl. No.: 227,045

[22] Filed: Aug. 1, 1988

[51] Int. Cl.[4] .............................. G01K 17/20
[52] U.S. Cl. ..................... 374/32; 324/105; 128/653; 343/703
[58] Field of Search ............... 374/31, 32; 343/703; 324/95, 105; 128/653; 250/250, 252.1 R

[56] References Cited

U.S. PATENT DOCUMENTS

| | | | |
|---|---|---|---|
| 3,147,439 | 9/1964 | Eakin | 325/364 |
| 3,394,258 | 7/1968 | Schleiger et al. | 250/83.3 |
| 3,639,841 | 2/1972 | Richardson | 325/363 |
| 3,790,794 | 2/1974 | Murray et al. | 374/32 |
| 4,167,109 | 9/1979 | Gold | 73/15 R |
| 4,185,497 | 1/1980 | Decker et al. | 374/32 |
| 4,611,166 | 9/1986 | Aslan | 324/95 |
| 4,659,984 | 4/1987 | Doss | 324/95 |
| 4,672,309 | 6/1987 | Gandhi | 324/95 |

FOREIGN PATENT DOCUMENTS 894622 12/1981 U.S.S.R.
991333 1/1983 U.S.S.R.

OTHER PUBLICATIONS

O. P. Gandhi et al., "Numerical and Experimental Results for Near Field Electromagnetic Absorption in Man," IEEE, Transactions on Microwave Theory and Techniques, vol. 30, No. 11, pp. 2000–2005, Nov. 1982.

Primary Examiner—William A. Cuchlinski, Jr.
Assistant Examiner—Scott Alyea
Attorney, Agent, or Firm—Harvey A. David; William C. Townsend

[57] ABSTRACT

Method and apparatus for use in measuring SAR (Specific Absorption Rate) of persons subject to RF (radio frequency) radiation utilizes twin well calorimetry including first and second gradient-layer type calorimetry boxes the thermally conductive walls and cover of which contain a multiplicity of thermocouples the outputs of which are differentially amplified to provide a differential output. Identical body models that are thermally responsive to RF radiation are contained in the box wells and, after a period of thermal equalization outside the influence of the RF source, one body model is removed from its well and placed in the influence of the radiation in question while the other remains outside the influence. After a predetermined time period the irradiated model is returned to its well and the differential outputs is plotted over a time period. The area under the resultant curve is representative of total absorption from which can readily be calculated SAR.

3 Claims, 2 Drawing Sheets

NEAR-FIELD RADIO WAVE DOSIMETRY

BACKGROUND OF THE INVENTION

This invention relates to the field of near-field, radio frequency (RF) irradiation dosimetry, and more particularly to provision of a practical and field-usable method and apparatus for determining potentially hazardous electromagnetic radiation near radio frequency emanating devices such as transmitting antennas, RF plastic welders, and the like.

Certain standards have been set for allowable levels of RF radiation of persons and, while these may change from time-to-time as more is learned abut the effects or hazards of radiation, there exists a need for suitable means to carry out accurate and reliable measurements of the near-field specific absorption rate (SAR) of persons subjected to radiation by non-ionizing radio frequency radiation (RFR) in the frequency range from 10 KHz to 300 GHz. For example, one standard limits an allowable SAR, in watts per kilogram, for a localized point of measurement or "hot spot" to 8.0 W/kg averaged over any 1 gram of tissue, and an average SAR of 0.4 W/kg for the whole body averaged over any 6 minute period. A variety of transmitting antennas are used on board ships and are often located in or near areas that are accessible to personnel who may be subject to radiation greater than are believed safe. Moreover, especially in shipboard and other areas where a variety of conductive structures abound, unintentionally tuned or resonant conditions may exist that cause RF radiation at locations other than at the principal emitter and hence produce an unexpectedly hazardous situation.

Prior methods and means for measurement of radiation have included implantable E-field (electric field) probes and thermal probes, the latter relying on the known fact that tissue temperature rise is related to absorbed RF radiation. These devices are subject to a number of limitations that make whole body SAR assessment very difficult. These limitations include inability of prior art probes and their associated instrumentation to integrate accurately the irradiation variables over the entire body mass of a person subjected to a variety of primary and secondary radiation sources.

SUMMARY OF THE INVENTION

With the foregoing in mind, the present invention has as a primary object the measurement of whole body SAR through use of a twin-well calorimeter apparatus in combination with a pair of body models having SAR/temperature characteristics that mimic those of a person.

Another object is to provide apparatus that allows for positioning of a body model in place of a human subject at an actual work station or other location of interest under actual conditions for evaluating compliance with electromagnetic radiation safety standards.

Other objects and many of the attendant advantages will be readily appreciated as the subject invention becomes better understood by reference to the following detailed description, when considered in conjunction with the accompanying drawings.

DESCRIPTION OF THE PREFERRED EMBODIMENT

Figure 1:
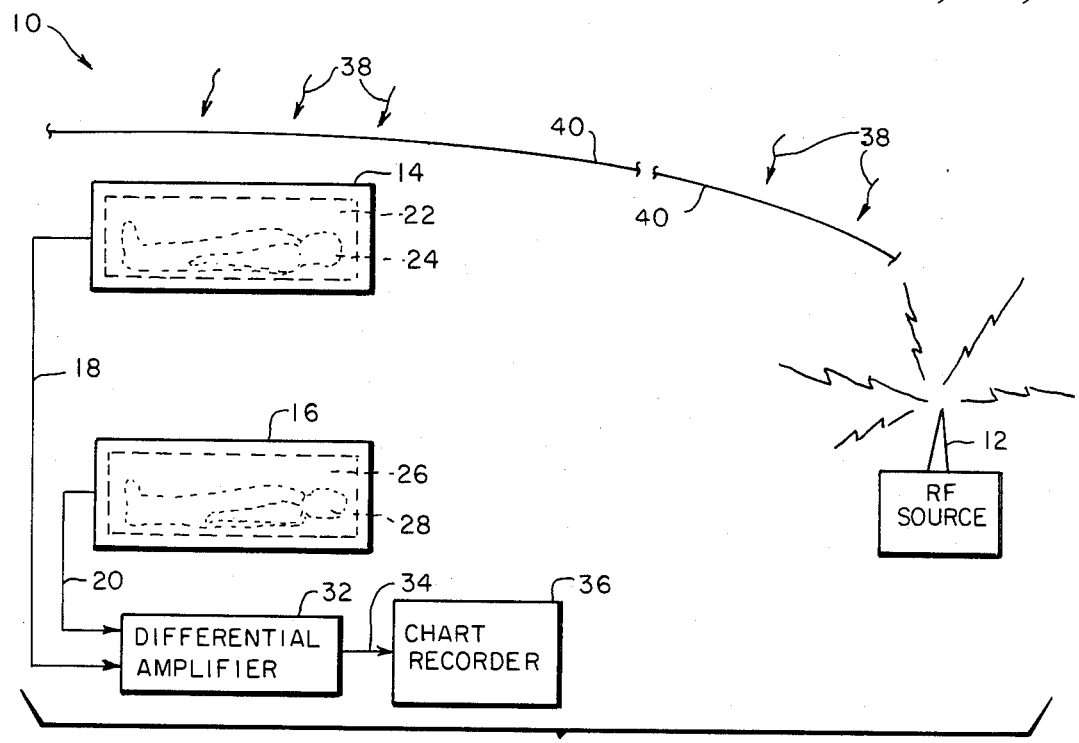
FIG. 1 is a diagrammatic illustration, partly in block form, of a twin well calorimetric dosimetry apparatus embodying the invention with body models in their respective wells.

Referring now to FIG. 1, an exemplary twin-well calorimetric dosimetry apparatus, shown generally at 10, is used to measure the SAR that would be experienced by a person subjected to RF radiation from an antenna 12 driven by an RF source.

The twin well calorimetric apparatus 10 comprises first and second gradient-layer type calorimeter boxes 14 and 16, each having thermally conductive walls and a cover. In accordance with conventional construction, the inner surfaces of the walls and covers of the boxes 14 and 16 contain a multiplicity of temperature sensors, e.g., thermocouples (not shown) that are electrically connected with one another and to pairs of D.C. output leads represented respectively by flow lines 18 and 20. Box 14 defines a first calorimeter well 22 which is of a size that will receive a first or subject body model 24, while box 16 defines a second calorimeter well 26 in which can be disposed a second or reference man model 28. The identical body models 24 and 28 form part of the apparatus 10 and comprise plastic film bags in the full scale configuration of a person and filled with a gel having mass, electrical, and specific heat characteristics representative of human tissue. The output leads 18,20 are appropriately shielded and provide D.C. voltage outputs representative of the average thermal outflows, if any, from the respective body models. These outputs are applied to a differential amplifier means 32 to provide a differential voltage output, line 34. The output 34 is applied to a chart recorder 36, or other recording and/or display means, which is conveniently calibrated in millivolts vs time. By virtue of the nature of gradient-layer calorimeters, the voltage output 34 is proportional to the net heat flow rate (in joules per second) necessary to achieve thermal equilibrium between the two calorimeters. Both calorimeter boxes are provided protection from the effects of direct solar radiation 38 and other thermally important factors that might influence the calorimeter unequally. A simple overhead protection device is shown at 40 as a tent.

In use, the apparatus is set up as shown in FIG. 1 and allowed to stabilize with both calorimeter boxes 14 and 16, and their respective body models 24 and 28, located at a distance remote enough from the antenna 12 to be outside its practical sphere of influence. Typical procedure for the whole body SAR measurement of an irradiated man model would be to initially allow both models to thermally equilibrate (come to the same temperature) by storing them in the same thermal environment (such as inside the two calorimeter wells) for at least 24 hours.

Figure 2:
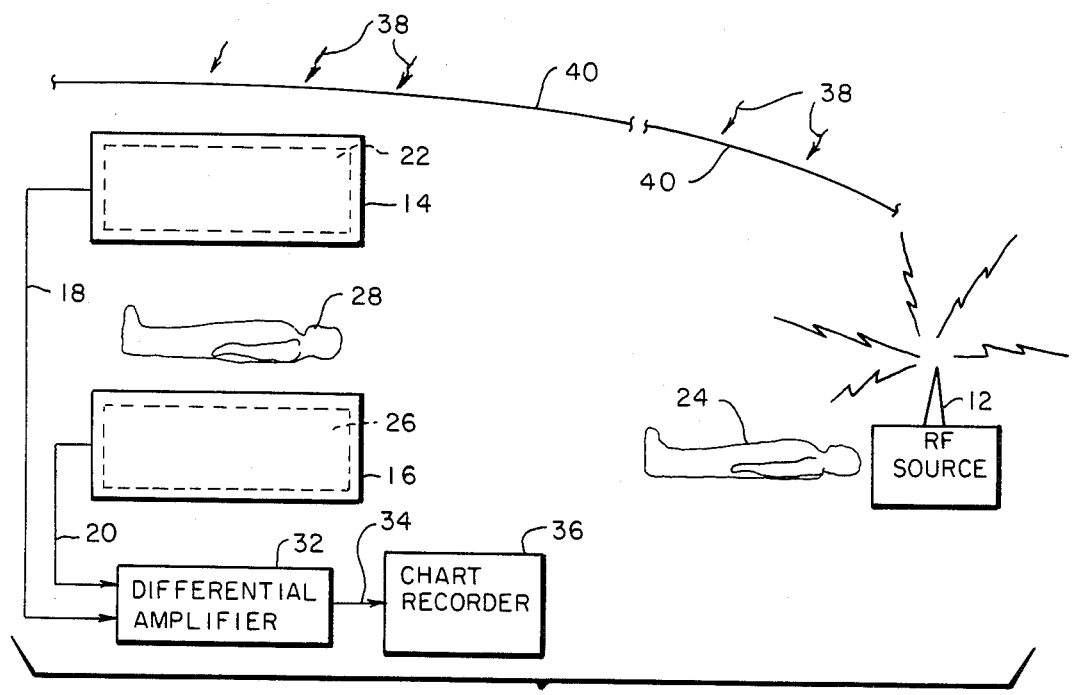
FIG. 2 is a view similar to FIG. 1 but with body models disposed as during an irradiation period.

One model, i.e. 24, is then removed from its well and subjected to a timed irradiation by placing it in a location of interest near antenna 12, as shown in FIG. 2, while the other model, 28, remains in as nearly the same thermal environment as possible but sufficiently distant from the antenna to allow no irradiation produced thermal accumulation. Immediately after irradiation, both models are returned or placed into the wells of calorimeter boxes 14 and 16, again remote from antenna 12 as shown in FIG. 1, where they remain until they again are at the same temperature, approximately 48 hours later.

Figure 3:
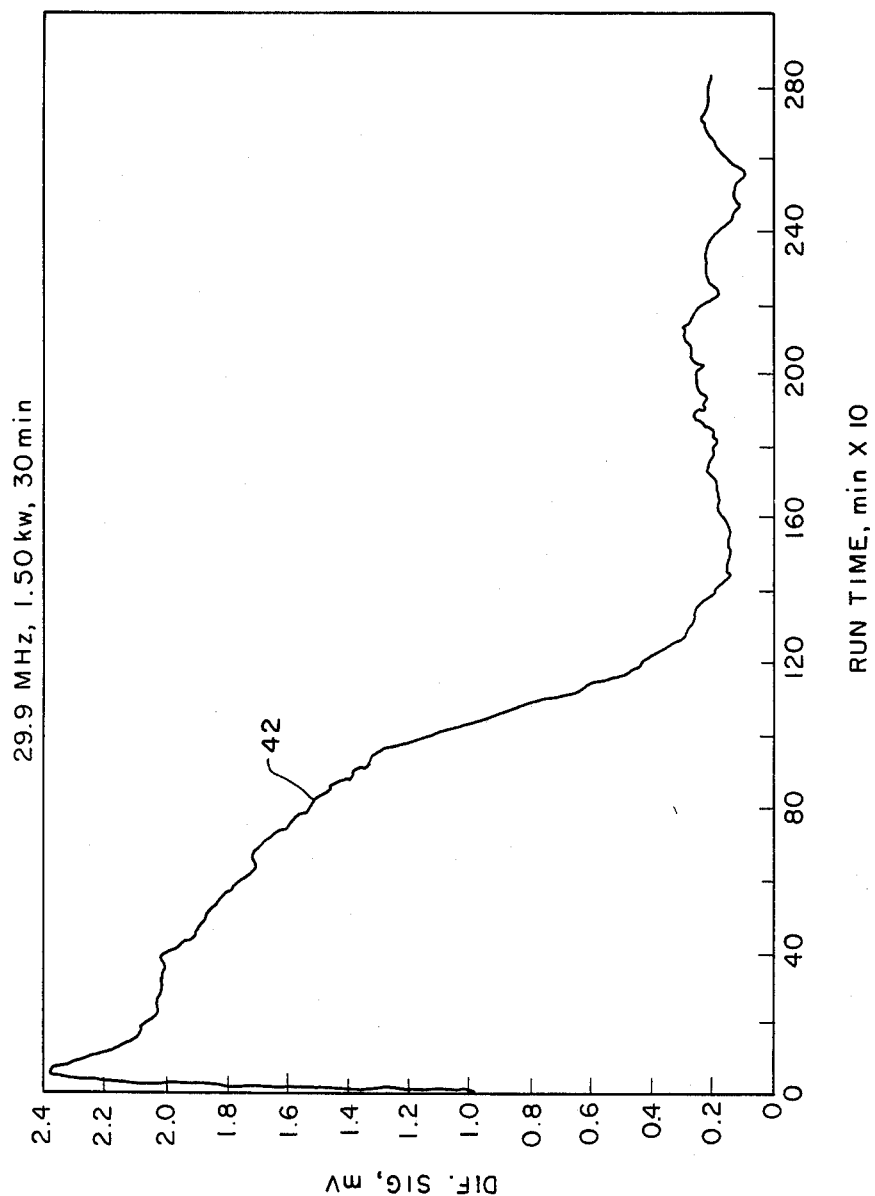
FIG. 3 illustrates an exemplary recorder trace generated by the apparatus of FIG. 1.

Referring to FIG. 3, 42 is a trace from the recorder 36 during the 48 hour period following the irradiation. In this example the model 24 had been irradiated with antenna 12 operating at 29.9 MHz 1.05 kW. The area under the curve represents RF radiation absorption in joules. SAR is calculated as the joules of absorbed energy divided by the irradiation period (in seconds) and further divided by the mass (in kilograms) of the irradiated model. SAR is, therefore, expressed as Watts per Kilogram.

This apparatus permits accurate determination of total body SAR to be expected in a human subject at a certain location relative to one or more antenna or other RF radiating devices or piece of gear. Moreover, it avoids limitations and problems inherent in using thermal or RF responsive probes.

Obviously, other embodiments and modifications of the subject invention will readily come to the mind of one skilled in the art having the benefit of the teachings presented in the foregoing description and the drawing. It is, therefore, to be understood that this invention is not to be limited thereto and that said modifications and embodiments are intended to be included within the scope of the appended claims.

What is claimed is:

1. Calorimetric dosimeter apparatus for use in determining the specific absorption rate (SAR) that would be experienced by a person exposed to radio frequency (RF) irradiation when in a predetermined location relative to one or more RF sources, said apparatus comprising:

first and second body models, each comprising a plastic film bag in the configuration of a person and filled with a gel having mass, electrical, and specific heat characteristics representative of human tissue;

calorimeter box means defining first and second wells for receiving said first and second body models after only one body model has been exposed to said RF irradiation at said predetermined location for which the SAR is to be determined, said box means having first and second electrical conductor means for providing first and second electrical signals corresponding to thermal outflows from said first and second body models, respectively, when in their respective wells;

differential amplifier means, responsive to said first and second electrical signals, for providing a differential output signal representative of the differential in said thermal outflows; and recorder means, responsive to said differential output signal for recording thereof as a function of time.

2. Calorimetric apparatus as defined in claim 1, and further comprising:

means for shielding said calorimeter box means from environmental conditions that would affect the temperature of said body models at a location remote from said predetermined location.

3. A method for determining specific absorption rate (SAR) for a person at a predetermined location subject to radio frequency (RF) irradiation by one or more RF sources, said method comprising the steps of:

providing first and second body models, each having the general configuration of said person and characterized by mass, electrical, and specific heat characteristics representative of human tissue;

allowing said first and second body models to reach thermal equilibrium relative to each other while at a remote location away from effects of said one or more RF sources;

moving one of said body models from said remote location to said predetermined location for RF irradiation over a first predetermined time period by said one or more RF sources;

returning said one of said body models to said remote location immediately after said RF irradiation; and measuring total thermal outflow differential of said one body model relative to the other body model over a second predetermined time period as representative of said RF irradiation.

* * * * *